United States Patent [19]

Abrams

[11] Patent Number: 5,078,673
[45] Date of Patent: Jan. 7, 1992

[54] SELECTIVE REMOVAL OF RADIOLABELED ANTIBODIES

[75] Inventor: Paul G. Abrams, Seattle, Wash.

[73] Assignee: NeoRx Corporation, Seattle, Wash.

[21] Appl. No.: 328,827

[22] Filed: Mar. 27, 1989

Related U.S. Application Data

[63] Continuation-in-part of Ser. No. 270,144, Nov. 14, 1988, abandoned.

[51] Int. Cl.$^5$ .................................. A61N 5/00
[52] U.S. Cl. ................................ 600/3; 604/4; 128/659
[58] Field of Search ............... 128/653, 654, 659; 600/1-6; 604/4-6, 19, 20, 27, 28; 424/1.1, 985.8; 436/547, 548

[56] References Cited

U.S. PATENT DOCUMENTS

| | | | |
|---|---|---|---|
| Re. 31,712 | 10/1989 | Giese | 604/29 |
| 4,182,780 | 1/1980 | Sullivan | 604/8 |
| 4,444,744 | 4/1984 | Goldenberg | 128/659 |
| 4,454,106 | 6/1984 | Gansoweld | 600/3 |
| 4,540,401 | 9/1985 | Marten | 604/28 |
| 4,563,170 | 1/1986 | Aigner | 604/27 |
| 4,605,394 | 8/1986 | Skurkovich | 604/5 |
| 4,624,846 | 11/1986 | Goldenberg | 128/659 |
| 4,681,870 | 7/1987 | Balint, Jr. et al. | |
| 4,687,808 | 8/1987 | Jarett et al. | 604/4 |
| 4,711,839 | 12/1987 | Singhal | |
| 4,737,544 | 4/1988 | McCain et al. | 604/5 |
| 4,820,261 | 4/1989 | Schmoll et al. | 604/5 |
| 4,896,780 | 7/1989 | Freed et al. | 604/4 |

FOREIGN PATENT DOCUMENTS

| | | |
|---|---|---|
| 0272792 | 6/1988 | European Pat. Off. . |
| 0273566 | 7/1989 | European Pat. Off. . |

OTHER PUBLICATIONS

Sinitsyn et al., "Rapid Blood Clearance of Biotinylated IgG After Infusion of Avidin", *J. Nucl. Med.*, vol. 30, No. 1, pp. 66-69 (1989).

*Primary Examiner*—David J. Isabella
*Assistant Examiner*—K. M. Reichle
*Attorney, Agent, or Firm*—Stoel Rives Boley Jones & Grey

[57] ABSTRACT

Methods of treating and imaging tumor sites using radiolabeled antibodies or fragments of antibodies are disclosed. Ex vivo separation of the radiolabeled antibodies is undertaken to improve image quality and treatment efficacy.

32 Claims, No Drawings

SELECTIVE REMOVAL OF RADIOLABELED ANTIBODIES

BACKGROUND OF THE INVENTION

This application is a continuation-in-part application of U.S. patent application Ser. No. 270,144, which was filed on Nov. 14, 1988 now abandoned.

Radiolabeled antibodies were first used successfully to treat a human cancer in 1952 (Vial and Callahan, *Univ. Mich. Med. Bull.* 20: 284–6, 1956). Typically, antibodies are radiolabeled with a radionuclide via a chelate molecule, but problems associated with each component of the three component immunoconjugate have been noted. The problems of insufficiently stable radionuclide chelates, inappropriate radionuclides, insufficiently specific antibodies, and altered antibody immunoreactivity after radiolabeling have been resolved through the use of improved chemical chelates, superior radionuclides, monoclonal antibodies and gentle conjugation techniques, respectively (Fritzberg et al., *PNAS* 85 4025–29, 1988).

Radionuclides are imaging and therapeutic agents of particular interest for use in antibody delivery systems, since the particles and energies emitted by radionuclides traverse one or more cells (Humm, *J. Nucl. Med.* 27: 1490–97, 1986). Thus, not every tumor cell need express the target antigen nor bind an antibody in order to be killed. This benefit however is mitigated by potential toxicity to normal cells caused by particle emissions from the conjugate as it traverses normal organs in the blood. This effect may be termed "innocent bystander" toxicity.

According to general pharmacological principles, delivery of an injected substance to organs and target sites is directly related to the concentration of the substance in the recipient's serum over time. This concentration is referred to as "concentration X time" or "area-under-the-curve" (AUC). Concentration values may be predicted, but are usually empirically derived and plotted over time.

Generally, the greater the "concentration X time" of a drug, the higher the amount of drug that will be delivered to a target. However, achieving an increased "concentration X time" of a drug that does not have specific target localization capability has certain drawbacks. While greater amounts of drug may be delivered to the particular tumor target, there will also be increased delivery to non-targeted, normal organs, because such drugs do not have a mechanism for differential delivery to the target. The higher the dose or, more accurately, the greater the AUC, the more potent and more toxic the chemotherapeutic drug. With untargeted drugs, this toxicity limits the ability to deliver more drug to a target tumor simply by increasing the dose.

Targeting molecules such as antibodies as carriers of cytotoxins partially ameliorate this problem. Administration of an antibody-targeted agent offers the potential of selective delivery of the agent to a target, such as a tumor. If the targeting molecule is carrying a drug or other non-radioactive substance, increased delivery to tumor may be achieved simply by increasing the dose administered assuming no significant nonspecific uptake in normal tissues.

Unfortunately, if the targeting molecule is carrying radioactivity, this selectivity may not be manifest because of the innocent bystander toxicity caused by radioactive particles emitted from, e.g., radiolabeled antibodies in circulating blood perfusing normal organs. Thus, a method of increasing the tumor deposition of radiolabeled antibody by increasing AUC while diminishing toxicity by limiting innocent bystander toxicity to normal tissues is needed.

SUMMARY OF THE INVENTION

The present invention involves methods of treating or imaging tumor sites using radiolabeled antibodies or fragments of antibodies. By separating serum from the cellular elements contained therein, and reducing the titer of radiolabeled antibody or fragments thereof in the blood of the mammal, a larger dose of the radiolabeled antibody or fragment can be administered to a mammal with little or no increase in toxicity to normal tissues. For imaging purposes, the additional benefit of decreased background ("visual noise") in the generated image is also obtained.

DETAILED DESCRIPTION OF THE INVENTION

A first aspect of the present invention contemplates a method of treating tumor tissue sites in mammals comprising:

(a) infusing a therapeutically effective amount of radiolabeled antibody or a fragment thereof into said mammal;

(b) withdrawing blood from said mammal;

(c) separating cellular elements from said blood;

(d) reducing titer of radiolabeled antibody or fragments thereof in serum of said mammal;

(e) infusing an amount of serum or serum substitute sufficient to replace serum separated in step (c); and (f) monitoring response of said mammal to said infusion.

Treatment of the present invention involves infusion of radionuclide therapeutic agents conjugated to a targeting substance. Such treatment can be used with patients who display sufficient localization of labeled antibody or fragment in an imaging study so as to warrant a therapeutic attempt, or with patients who are diagnosed in any other manner. A determination of the feasibility of a therapeutic attempt would be based upon a predicted dose to the tumor for a given administered dose of radiolabeled antibody. Such feasibility determination may be made by a practitioner skilled in tumor chemotherapy and/or radiation oncology and/or nuclear medicine.

Infusions contemplated by the present invention may be conducted in any manner adequate to deliver the labeled antibody or antibody fragment to the bloodstream of the imaging patient. Exemplary of acceptable administration routes are intraperitoneal, subcutaneous, intradermal, intraarterial or intravenous injection. The mode of administration will be chosen according to the projected ultimate destination of the labeled antibody, i.e. the tumor location. Such infusions may be given as single or multiple injections.

In vivo administration of labeled antibody or fragment thereof may involve the use of pharmaceutical compositions in which the labeled antibody is dispersed in a pharmaceutically acceptable carrier. Exemplary of such a pharmaceutically acceptable carrier is physiological saline.

Exemplary of radiolabels useful in the present invention are radionuclides, and labeling may be done by conventional techniques (Abrams et al., *Principles of*

*Cancer Biotherapy,* R.K. Oldham ed., 1987, Raven Press Ltd., New York, pp. 337–54). Alvarez et al. suggest further methodologies for such labeling in U.S. Pat. No. 4,741,900.

Radionuclides useful within the present invention include gamma-emitters, positron-emitters, Auger electron-emitters, X-ray emitters and fluorescence emitters, with beta- or alpha-emitters preferred for therapeutic use. Exemplary radionuclides are well-known in the art and include $^{111}$In, $^{51}$Cr, $^{188}$Re, $^{186}$Re, $^{198}$Au, $^{199}$Ag, $^{123}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{105}$Rh, $^{119}$Sb, $^{128}$Ba, $^{197}$Hg, $^{211}$At, $^{212}$Bi, $^{203}$Pb, $^{212}$Pb, $^{109}$Pd, $^{67}$Ga, $^{68}$Ga, $^{64}$Cu, $^{67}$Cu, $^{97}$Ru, $^{75}$Br, $^{76}$Br, $^{77}$Br, $^{99m}$Tc, $^{11}$C, $^{13}$N, $^{15}$O and $^{18}$F. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au, and $^{199}$Ag.

The term "antibody" as used in the present invention encompasses polyclonal and monoclonal antibodies. Moreover, the term "antibody" encompasses whole antibody and antibody fragments capable of binding to a particular target. Exemplary antibody fragments include F(ab')$_2$, Fab', Fab or Fv.

Whole antibody ordinarily remains in the circulation 24 hours or longer. This extended time that whole antibody circulates prior to blood clearance increases the risk of bone marrow and other normal organ toxicity when therapeutic radionuclides are used.

However, use of whole antibody may be preferable over use of antibody fragments, since the fragments, which ordinarily have more rapid blood clearance than whole antibody, accumulate in the kidney which may be the principal organ suffering toxicity as a result of therapeutic applications using antibody fragments as targeting agents.

The method of this invention obviates this problem and allows the use of labeled whole antibody, because the separation and reducing steps of the method decrease the time that whole antibody is in circulation. An additional benefit of conducting the separation and reducing steps in accordance with the present invention is a decrease in renal accumulation of antibody fragments, thereby increasing the usefulness of fragment delivery systems for therapy.

Such antibody or antibody fragments may be made according to conventional techniques, such as production from hybridoma cells, recombinant DNA techniques and protein synthesis. Antibodies or antibody fragments may be derived from any species (including humans) or may be chimeric proteins which employ sequences from more than one species (Kohler and Milstein, *Nature* 256: 495–97, 1975; *Eur. J. Immunol.* 6: 511–19, 1976).

Antibodies or antibody fragments useful in the present invention may bind to a tumor-associated antigen, differentiation antigens, specific receptors or any cell surface or internal site that results in preferential localization of the antibody in tumor, rather than normal, tissues. Antibodies or fragments having little or no overlapping cross-reactivity with normal tissues may be used in "cocktails" to decrease the exposure of any single vital normal organ to the full dose of labeled antibody. A "cocktail" contains two or more distinct antibodies or antibody fragments that are coupled to identical or non-identical diagnostic or therapeutic agents. See, for example, copending U.S. patent application, Ser. No. 160,648.

The separation and reducing steps of the present methods may be accomplished by application of standard plasmapheresis techniques. In an exemplary technique, venous access is established with a large gauge needle, and blood is withdrawn by pumping through tubing from the subject into a centrifuge. Within the centrifuge, different densities of serum, white blood cells, red blood cells and platelets facilitate separation of these blood elements. For the purposes of the present invention, it is sufficient to separate serum from cellular components as a whole. The separated cells are immediately returned to the patient by a second intravenous line.

Several techniques can be performed to reduce the titer of radiolabeled antibody in the blood of the mammal. An exemplary reducing step in accordance with the present invention contemplates that the withdrawn and separated serum is discarded and replaced with intravenous fluids and volume expanders, thereby diluting out the labeled antibody.

Another exemplary reducing step involves passing the withdrawn and separated serum through an affinity column to remove the infused radiolabeled antibody selectively prior to reinfusion of the patient's serum. The separated serum may be processed by passage (1) through a single affinity column one or more times, or (2) through several affinity columns arranged serially. The number of passes, number of columns, and size of the column or columns used will depend on the specificity and affinity of the anti-antibody bound to the column, as well as on the dose of labeled antibody infused into the patient. A practitioner versed in serum purification would be able to determine an appropriate removal scheme. Upon completion of affinity chromatography of the separated serum (i.e., upon completion of the removal step of the method), the eluted serum is reinfused into the patient through a second intravenous line.

An affinity column useful in the present invention may be made by standard techniques, and may employ antibodies or fragments thereof directed against the idiotype, subclass, isotype or species of the labeled antibody or the target antigen. The efficiency of this type of removal process increases as the specificity of the affinity antibody for the labeled antibody increases, since less endogenous antibody will cross-react with the affinity antibody and be coadsorbed. Also, antigen directed against the labeled antibody or antibody fragment may be used in the affinity column to remove the labeled antibody or fragment thereof.

Preferred affinity matrixes incorporate antibodies having high affinity for the labeled antibody or fragment. In a particularly preferred embodiment, an affinity column contains an antibody having an affinity on the order of about $10^{-8}$ M/1 or greater. With such high affinity antibody, the efficiency of the removal process will be enhanced because increased amounts of labeled antibody will be removed by each pass through the column.

Alternatively, the antibody employed in the affinity column may be directed against the radionuclide chelate. An anti-chelate affinity column would be more efficient than an anti-antibody affinity column, since unlabeled antibody would not be co-adsorbed. In addition, radiolabeled antibodies derivatized with more than one chelate would be more efficiently removed by an anti-chelate column (as compared to antibodies with only one chelate per molecule). In this instance, smaller capacity affinity columns may be used, since the absolute number of molecules removed from serum would be decreased. Moreover, an anti-chelate affinity matrix permits the removal of circulating radioactive metabolites, such as radiolabeled peptides, so long as the chelate itself remains intact.

Generally, the amount of labeled antibody or fragment thereof administered to a patient will depend primarily on the size of the patient. However, the patient's physiological condition and the tissue site to be treated or imaged (if known) may affect the amount of labeled antibody necessary to obtain a usable image.

A typical dose of radiolabeled antibody is between about 1 and about 3000 mCi. Dosage of labeled antibody for imaging purposes may readily be determined by one of ordinary skill in diagnostic imaging. In humans, the standard dose will be about 50 to about 2000 mCi for therapeutic purposes, with about 50 to about 700 mCi being typical.

The time lapse between infusion of the labeled antibody or fragment and separation/reduction may be established by determining the physical half-life of the imaging radionuclide and the signal-to-noise ratio required to image tumors of various sizes. For example, Fab fragments localize more quickly in tumors than whole antibody. A nuclear medicine practitioner would be able to calculate the dose to the tumor by region of interest analysis before and after plasmapheresis. By performing this analysis at several time points with a series of patients, an optimal range of time for plasmapheresis may be ascertained.

For whole antibody, separation/reduction would be performed between about 6 and about 48 hours following infusion of labeled antibody, with a time lapse between about 6 and about 24 hours being preferred. For F(ab')$_2$, the time lapse between infusion and separation/reduction would be between about 2 and about 15 hours, with between about 8 and about 15 hours being preferred. For Fab', Fab and Fv, this time lapse would be between about 1 and about 20 hours, with between about 3 and about 8 hours being preferred.

If normal tissue expression of the antigen or determinant recognized by the labeled antibody is less than the tumor expression of this antigen or determinant, normal tissue sites may be saturated before the tumor sites are filled. Such saturation of normal tissue may result in toxicity to normal tissue due to the presence of the radiolabel. Pre-infusion of non-labeled antibody or antibody fragment prior to infusing its labeled counterpart may improve localization of labeled antibody in the tumor area. The preinfused, "cold" antibody will migrate to the most readily accessible cells bearing the recognized antigen or determinant. Where normal tissue sites bearing the recognized antigen or determinant are more accessible to the labeled antibody than analogous sites on tumor tissue, a pre-infusion step may be beneficial. See, for example, co-pending U.S. patent application, Ser. No. 917,176.

For example, antigen-bearing normal cells within the bloodstream will be more accessible to "cold" antibody than non-circulating tumor tissue cells. This "cold" agent will associate preferentially with the more accessible, peripheral, antigen-bearing normal cells. As a result, subsequently infused labeled or "hot" antibody will be more likely to reach and bind the less accessible, antigen-bearing tumor cells. Since "cold" antibody does not bear the radioactive toxic label, normal tissue damage will be reduced. On the other hand, if a significant, accessible normal tissue antigen pool does not exist, no pre-infusion is necessary.

For "cold" infusion, a non-labeled antibody or fragment is infused into a patient whose tissue sites are to be treated in the same or different manner than is the labeled antibody or fragment. In vivo administration of non-labeled antibody or fragment may involve the use of pharmaceutical compositions in which dispersion in a pharmaceutically acceptable carrier is necessary or desirable. Exemplary of such a pharmaceutically acceptable carrier is physiological saline.

Generally, the amount of non-labeled antibody or fragment administered to a patient will depend primarily on the size of the patient. However, the patient's physiological condition and the tissue site to be treated or imaged, if known, may impact the amount of non-labeled antibody required to obtain a diagnostic image substantially free of background. Dosage of non-labeled antibody may readily be determined by one of ordinary skill in diagnostic imaging. The time lapse between infusion of non-labeled antibody and labeled antibody will vary somewhat with the patient's characteristics (i.e., body weight) and condition, as well as with the administration route, antibody and label used. The time lapse necessary to allow the non-labeled antibody or fragment adequate opportunity to associate with normal cells is readily determinable by a person ordinarily skilled in diagnostic imaging.

A second aspect of the present invention involves a method of imaging tumor tissue sites in mammals comprising:

(a) infusing an amount of radiolabeled antibody or a fragment thereof sufficient to obtain a diagnostic image;

(b) withdrawing blood from said mammal;

(c) separating cellular elements from said blood;

(d) reducing titer of radiolabeled antibody or fragments thereof in blood of said mammal;

(e) infusing an amount of serum or serum substitute sufficient to replace blood volume lost in separating step (c); and (f) imaging said tissue site, whereby medical conditions involving tumor tissue sites may be detected, evaluated and monitored.

By imaging there is contemplated conventional diagnostic in vivo imaging. Briefly, a substance capable of detection by external means, i.e. a labeled substance, is administered to a patient in an amount sufficient to deliver an adequate supply of labeled substance to the target tissue to permit an image to be generated. Radionuclides are typically coupled with a targeting substance to achieve this end. The radionuclide provides the imaging input, while the targeting substance provides the targeting capability of the radiolabeled conjugate.

The imaging of the present invention may be accomplished with the aid of one of the many commercially available imaging cameras, such as the Picker Digital Dynascan camera, the Raytheon LFOV Anger gamma camera and the gamma camera STARCAM made by General Electric Corporation. Images may be obtained during the course of therapeutic scanning techniques, such as planar nuclear or single photon emission computed tomographic (SPECT) scans.

As discussed previously, whole antibody ordinarily remains in the circulation 24 hours or longer, resulting in the creation of background "visual noise" upon imaging. The accumulation of labeled antibody in areas other than at the target tissue site will decrease the clarity of the image in much the same way as background noise clutters an audio signal.

However, use of whole antibody may be preferable over use of antibody fragments, since the fragments, which ordinarily have more rapid blood clearance than whole antibody, accumulate in the kidney and obscure that area upon imaging. The imaging method of the present invention has the advantage of permitting whole antibody to be used, absent the clearance problems typically associated with its use. Moreover, should "visual noise" in images produced according to the present invention result in part from normal tissue expression of the antigen or determinant recognized by the labeled antibody, "cold" antibody may be administered to the imaging patient prior to labeled antibody.

In humans, the standard dose will vary according to the radionuclide by generally from about 1 to about 50 mCi for imaging purposes, with about 10 to about 30 mCi being typical. Dosage of labeled antibody for therapeutic purposes may readily be determined by a doctor versed in nuclear medicine.

Diagnostic imaging in accordance with the present invention may be performed after the separation/reduction, or even during the procedure, if a camera is conveniently placed in the room with the separation/reduction apparatus.

Images produced according to the present invention may aid in the detection of tumor tissue or tumor metastases. A diagnostician will recognize image patterns characterizing such tumor sites. Also, the images produced according to the present invention will provide the diagnostician with information regarding the extent of that tumor tissue infiltration. As a result, a sequence of images of an afflicted tissue site produced at different times will permit monitoring of treatment protocols designed to alleviate that tissue infiltration.

A third aspect of the present invention involves a method of treating tumor tissue sites in mammals including:

(a) biotinylating or avidinlyating and radiolabeling an antibody or a fragment thereof;

(b) infusing a therapeutically effective amount of biotinylated or avidinylated, radiolabeled antibody or a fragment thereof into the mammal;

(c) withdrawing blood from the mammal;

(d) separating cellular elements from the blood;

(e) reducing titer of radiolabeled antibody or fragments thereof in serum of the mammal; and (f) infusing an amount of serum, serum substitute or both sufficient to replace serum separated in step (d).

By biotinylating, there is contemplated a linkage of biotin to amino or carbohydrate residues located on the antibody or antibody fragment. Biotin may be linked to an antibody in a ratio from 1:1 to 1:100 (antibody:biotin). Preferably, biotin may be linked to an antibody in a ratio from 1:1 to 1:30. Biotin and methods of biotinylation are known. See, for example, Hoffmann et al., *Proc. Natl. Acad. Sci. USA*, 74:2697–2700 (1977). Techniques of antibody radiolabeling are also known, as discussed above.

Similarly, by avidinylating, there is contemplated linkage of avidin to the antibody or antibody fragment. The parameters of such linkage are substantially as described in for biotinylation above.

In this aspect of the present invention, the reducing step (e) involves passing the withdrawn and separated serum through an affinity column to remove the infused biotinylated or avidinylated, radiolabeled antibody selectively prior to reinfusion of the patient's serum. The separated serum may be processed by passage (1) through a single affinity column one or more times, or (2) through several affinity columns arranged serially. The number of passes, number of columns, and size of the column or columns used will depend on such parameters such as the dose of labeled antibody infused into the patient. A practitioner versed in serum purification would be able to determine an appropriate removal scheme. Upon completion of affinity chromatography of the separated serum (i.e., upon completion of the removal step of the method), the eluted serum is reinfused into the patient through a second intravenous line.

An affinity column useful in the present invention may be made by standard techniques, and will employ avidin if the antibody or fragment to be administered to a mammal is biotinylated. Avidin is known to interact with biotin both *in vivo* and *ex vivo*. See, for example, Sinitsyn et al., *J. Nucl. Med.*, 30(1):66–69 (1989). Thus, avidin bound to the affinity column will selectively remove the biotinylated antibodies or antibody fragments from the serum passing through.

Similarly, an affinity column useful in the present invention will employ biotin if the antibody or fragment to be administered to a mammal is avidinylated. The biotin bound to the affinity column will selectively remove the avidinylated antibodies or antibody fragments from the serum passing through.

In another aspect of the present invention, there is contemplated a method of imaging tumor tissue sites in mammals involving:

(a) biotinylating or avidinylating and radiolabeling an antibody or a fragment thereof;

(b) infusing an amount of biotinylated or avidinylated, radiolabeled antibody or a fragment thereof sufficient to obtain a diagnostic image;

(c) withdrawing blood from the mammal;

(d) separating cellular elements from the blood;

(e) reducing titer of radiolabeled antibody or fragments thereof in serum of said mammal;

(f) infusing an amount of serum, serum substitute or both sufficient to replace blood volume lost in separating step (d); and (g) imaging the tissue site, whereby medical conditions involving tumor tissue sites may be detected, evaluated and monitored.

To summarize the examples that follow, Example I describes a method of imaging a tumor tissue site in accordance with the present invention; Example II describes a method of treating a tumor tissue site in accordance with the present invention; and Example III describes methods of imaging and treating a tumor tissue site in accordance with the present invention. Example IV describes a method of treating a tumor tissue site in accordance with the third aspect of the present invention. Example V describes a method of imaging a tumor tissue site in accordance with the fourth aspect of the present invention. These examples are offered as illustrations of the present invention, not as limitations thereof.

EXAMPLE I

Imaging of a Patient with Small Cell Lung Cancer Using NR-LU-10 Labeled With Technetium-99m A patient with biopsy-proven small cell lung cancer presents to a clinic for staging evaluation. Whole NR-LU-10 monoclonal antibody is labeled with Tc-99m via the diamide dithiolate ligand system described by Fritzberg et al., PNAS 85:4025-29 (1988). Labeled monoclonal antibody (30 millicuries of Tc-99m on 10 mg of antibody) is injected into the patient. Fifteen hours later, the patient undergoes plasmapheresis for two hours. The patient's plasma is filtered through an affinity column whose active ingredient is an anti-idiotype antibody directed against the NR-LU-10 idiotypic determinant. Following plasmapheresis, the patient undergoes gamma camera imaging. The patient's primary and metastatic tumors are detected by this procedure.

EXAMPLE II

Treatment of a Patient with Small Cell Lung Cancer Using NR-LU-10 Labeled With Rhenium-186

NR-LU-10 is radiolabeled with rhenium-186 via a diamide dithiolate ligand system as described in Example I. Radiolabeled monoclonal antibody (400 millicuries Re-186 on 150 mg of antibody) is administered to the patient of Example I by intravenous injection. After twenty-four hours, the plasmapheresis procedure of Example I is performed for three hours. In this manner, the patient's tumors receive a sufficient dose of radiation to cause a response, and the patient's bone marrow is spared the toxicity that would have been caused had the radiolabeled antibody been permitted to circulate until it was metabolized and excreted.

EXAMPLE III

Imaging and Treatment of a Patient with Small Cell Lung Cancer Using Labeled NR-LU-10

The procedures described in Examples I and II are performed using an affinity column with an active ingredient that is an antibody to the diamide dithiolate ($N_2S_2$) chelate of Technetium-99m-$N_2S_2$ and Rhenium-196-$N_2S_2$. Radiolabeled intact antibody and any circulating radiolabeled metabolites are removed through passage through the anti-chelate affinity column of this Example.

EXAMPLE IV

Treatment of a Patient with Small Cell Lung Cancer Using NR-LU-10 Labeled With Rhenium-186

NR-LU-10 is treated with NHS-biotin in accordance with Hoffmann et al., *Proc. Natl. Acad. Sci. USA*, 74:2697-2700 (1977). The molar ratio of NHS-biotin to antibody is 10:1. Biotinylated NR-LU-10 is labeled with Rh-186 via the diamide dithiolate ligand system described by Fritzberg et al., PNAS 85:4025-29 (1988). Labeled monoclonal antibody (400 millicuries of Rh-186 on 150 mg of antibody) is injected into the patient. Twelve hours later, the patient undergoes plasmapheresis for two hours. The patient's plasma is filtered through an affinity column whose active ingredient is avidin. Following plasmapheresis, the patient undergoes gamma camera imaging. The patient's primary and metastatic tumors are detected by this procedure.

EXAMPLE V

Imaging of a Patient with Small Cell Lung Cancer Using NR-LU-10 Labeled With Technetium-99m A patient with biopsy-proven small cell lung cancer presents to a clinic for staging evaluation. NR-LU-10 is treated with NHS-biotin in accordance with Hoffmann et al., *Proc. Natl. Acad. Sci. USA*, 74:2697-2700 (1977). Whole NR-LU-10 monoclonal antibody is labeled with Tc-99m via the diamide dithiolate ligand system described by Fritzberg et al., PNAS 85:4025-29 (1988). Labeled monoclonal antibody (30 millicuries of Tc-99m on 10 mg of antibody) is injected into the patient. Fifteen hours later, the patient undergoes plasmapheresis for two hours. The patient's plasma is filtered through an affinity column whose active ingredient is avidin. Following plasmapheresis, the patient undergoes gamma camera imaging. The patient's primary and metastatic tumors are detected by this procedure.

What is claimed is:

1. A method of treating tumor tissue sites in a mammal comprising:
   (a) infusing a therapeutically effective amount of radiolabeled antibody or a fragment thereof into said mammal;
   (b) withdrawing blood from said mammal;
   (c) separating cellular elements from said blood to produce a serum fraction and returning said cellular elements to said mammal;
   (d) reducing the titer of radiolabeled antibody or fragments thereof in said serum fraction of said mammal to produce purified serum;
   (e) infusing said purified serum into said mammal to replace said serum fraction separated in step (c); and
   (f) monitoring the response of said mammal to said infusion.

2. A method of claim 1, which further comprises the initial step of infusing unlabelled antibody into said mammal.

3. A method of claim 1, wherein reducing step (d) is accomplished by an affinity column.

4. A method of claim 3, wherein an anti-idiotype antibody or fragment thereof to the radiolabeled antibody or fragment thereof is bound to said affinity column to remove said radiolabeled antibody or fragment thereof.

5. A method of claim 3, wherein an anti-isotype antibody or fragment thereof to the radiolabeled antibody or fragment thereof is bound to said affinity column to remove said radiolabeled antibody or fragment thereof.

6. A method of claim 3, wherein an anti-species antibody or fragment thereof to the radiolabeled antibody or fragment thereof is bound to said affinity column to remove said radiolabeled antibody or fragment thereof.

7. A method of claim 3, wherein an anti-subclass antibody or fragment thereof to the radiolabeled antibody or fragment thereof is bound to said affinity column to remove said radiolabeled antibody or fragment thereof.

8. A method of claim 3, wherein an antigen directed to the radiolabeled antibody or fragment thereof is bound to said affinity column to remove said radiolabeled antibody or fragment thereof.

9. A method of claim 3, wherein an antibody directed against a radionuclide chelate is bound to said affinity column to remove said radiolabeled antibody or fragment thereof.

10. A method of claim 1, wherein reducing step (d) is accomplished by dilution.

11. A method of imaging tumor tissue sites in a mammal comprising:
   (a) infusing an amount of radiolabeled antibody or a fragment thereof sufficient to obtain a diagnostic image;
   (b) withdrawing blood from said mammal;

(c) separating cellular elements from said blood to produce a serum fraction and returning said elements to said mammal;

(d) reducing the titer of radiolabeled antibody or fragments thereof in said serum fraction of said mammal to produce purified serum;

(e) infusing said purified serum into said mammal to replace said serum fraction separated in step (c); and (f) imaging said tissue site, whereby medical conditions involving tumor tissue sites may be detected, evaluated and monitored.

12. A method of claim 11, which further comprises the initial step of infusing unlabelled antibody into said mammal.

13. A method of claim 11, wherein reducing step (d) is accomplished by an affinity column.

14. A method of claim 13, wherein an anti-idiotype antibody or fragment thereof to the radiolabeled antibody or fragment thereof is bound to said affinity column to remove said radiolabeled antibody or fragment thereof.

15. A method of claim 13, wherein an anti-isotype antibody or fragment thereof to the radiolabeled antibody or fragment thereof is bound to said affinity column to remove said radiolabeled antibody or fragment thereof.

16. A method of claim 13, wherein an anti-species antibody or fragment thereof to the radiolabeled antibody or fragment thereof is bound to said affinity column to remove said radiolabeled antibody or fragment thereof.

17. A method of claim 13, wherein an anti-subclass antibody or fragment thereof to the radiolabeled antibody or fragment thereof is bound to said affinity column to remove said radiolabeled antibody or fragment thereof.

18. A method of claim 13, wherein an antigen directed to the radiolabeled antibody or fragment thereof is bound to said affinity column to remove said radiolabeled antibody or fragment thereof.

19. A method of claim 13, wherein an antibody directed against a radionuclide chelate is bound to said affinity column to remove said radiolabeled antibody or fragment thereof.

20. A method of claim 11, wherein reducing step (d) is accomplished by dilution.

21. A method of treating tumor tissue sites in a mammal comprising:

(a) biotinylating or avidinylating and radiolabeling an antibody or a fragment thereof;

(b) infusing a therapeutically effective amount of biotinylated or avidinylated, radiolabeled antibody or a fragment thereof into said mammal;

(c) withdrawing blood from said mammal;

(d) separating cellular elements from said blood to produce a serum fraction and returning said cellular elements to said mammal;

(e) reducing the titer of radiolabeled antibody or fragments thereof in said serum fraction of said mammal to produce purified serum;

(f) infusing said purified serum into said mammal to replace said serum fraction separated in step (d); and (g) monitoring the response of said mammal to said infusion.

22. A method of claim 21, which further comprises the initial step of infusing unlabeled antibody into said mammal.

23. A method of claim 21, wherein reducing step (e) is accomplished by an affinity column.

24. A method of claim 23, wherein avidin is bound to said affinity column to remove said biotinylated, radiolabeled antibody or fragment thereof.

25. A method of claim 23, wherein biotin is bound to said affinity column to remove said avidinylated, radiolabeled antibody or fragment thereof.

26. A method of claim 21, wherein reducing step (e) is accomplished by dilution.

27. A method of imaging tumor tissue sites in a mammal comprising:

(a) biotinylating or avidinylating and radiolabeling an antibody or a fragment thereof;

(b) infusing an amount of biotinylated or avidinylated, radiolabeled antibody or a fragment thereof sufficient to obtain a diagnostic image;

(c) withdrawing blood from said mammal;

(d) separating cellular elements from said blood to produce a serum fraction and returning said cellular elements to said mammal;

(e) reducing the titer of radiolabeled antibody or fragments thereof in said serum fraction of said mammal to produce purified serum;

(f) infusing said purified serum into said mammal to replace said serum fraction separated in step; (d); and (g) imaging said tissue site, whereby medical conditions involving tumor tissue sites may be detected, evaluated and monitored.

28. A method of claim 27, which further comprises the initial step of infusing unlabeled antibody into said mammal.

29. A method of claim 27, wherein reducing step (e) is accomplished by an affinity column.

30. A method of claim 29, wherein avidin is bound to said affinity column to remove said biotinylated, radiolabeled antibody or fragment thereof.

31. A method of claim 29, wherein biotin is bound to said affinity column to remove said avidinylated, radiolabeled antibody or fragment thereof.

32. A method of claim 27, wherein reducing step (e) is accomplished by dilution.

* * * * *